US010411197B2

(12) United States Patent
Maltenberger et al.

(10) Patent No.: US 10,411,197 B2
(45) Date of Patent: Sep. 10, 2019

(54) MAIN GROUP METAL COMPLEXES AS P-DOPANTS FOR ORGANIC ELECTRONIC MATRIX MATERIALS

(71) Applicant: SIEMENS AKTIENGESELLSCHAFT, Munich (DE)

(72) Inventors: Anna Maltenberger, Leutenbach (DE); Marina A Petrukhina, Schenectady, NY (US); Guenter Schmid, Hemhofen (DE); Jan Hauke Wemken, Nuremburg (DE)

(73) Assignees: SIEMENS AKTIENGESELLSCHAFT, Munich (DE); OSRAM OLED GMBH, Regensburg (DE)

( * ) Notice: Subject to any disclaimer, the term of this patent is extended or adjusted under 35 U.S.C. 154(b) by 442 days.

(21) Appl. No.: 14/406,041

(22) PCT Filed: May 14, 2013

(86) PCT No.: PCT/EP2013/059911
§ 371 (c)(1),
(2) Date: Dec. 5, 2014

(87) PCT Pub. No.: WO2013/182389
PCT Pub. Date: Dec. 12, 2013

(65) Prior Publication Data
US 2015/0123047 A1 May 7, 2015

(30) Foreign Application Priority Data
Jun. 6, 2012 (DE) .................. 10 2012 209 523

(51) Int. Cl.
H01L 51/50 (2006.01)
H01L 51/56 (2006.01)
(Continued)

(52) U.S. Cl.
CPC ............ *H01L 51/0077* (2013.01); *C07F 9/94* (2013.01); *C09K 11/06* (2013.01); *H01L 51/002* (2013.01);
(Continued)

(58) Field of Classification Search
CPC ... H01L 51/002; H01L 51/007; H01L 51/506; H01L 51/0051; H01L 51/0058;
(Continued)

(56) References Cited

U.S. PATENT DOCUMENTS 4,622,355 A 11/1986 Arnold, Jr. et al.
5,247,226 A 9/1993 Sato et al.
(Continued)

FOREIGN PATENT DOCUMENTS

DE 102010041331 3/2012
DE 102012209523.3 6/2012
(Continued)

OTHER PUBLICATIONS

Evgeny V. Dikarev et al., "Tuning the Properties at Heterobimetallic Core: Mixed-Ligand Bismuth-Rhodium Paddlewheel Carboxylates," Journal of the American Chemical Society, vol. 128, No. 9, 2006, pp. 2814-2815.
(Continued)

Primary Examiner — Tri V Nguyen
(74) Attorney, Agent, or Firm — Slayden Grubert Beard PLLC

(57) ABSTRACT

A metal complex of a metal from groups 13 to 16 uses a ligand of the structure (I), where $R^1$ and $R^2$ can independently be oxygen, sulfur, selenium, NH or $NR^4$, where $R^4$ an alkyl or aryl and can be connected to $R^3$. $R^3$ is an alkyl, long-chain alkyl, alkoxy, long-chain alkoxy, cycloalkyl, halogenalkyl, aryl, arylene, halogenaryl, heteroaryl, heteroarylene, heterocycloalkylene, heterocycloalkyl, halogen-
(Continued)

heteroaryl, alkenyl, halogenalkenyl, alkynyl, halogenalkynyl, ketoaryl, halogenketoaryl, ketoheteroaryl, ketoalkyl, halogenketoalkyl, ketoalkenyl, halogenketoalkenyl, where in suitable radicals, one or more non-adjacent $CH^2$— groups can be substituted independently of one another by —O—, —S—, —NH—, —NR°—, —SiR°R°°—, —CO—, —COO—, —OCO—, —OCO—O—, —$SO_2$—, —S—CO—, —CO—S—, —CY1=CY2 or —C≡C—, specifically in such a way that O and/or S atoms are not connected directly to one another, are likewise optionally substituted with aryl- or heteroaryl preferably containing 1 to 30 C atoms, as a dopant for matrix materials in organic electronic components.

19 Claims, 8 Drawing Sheets

(51) Int. Cl.
   *H01L 51/00* (2006.01)
   *C07F 9/94* (2006.01)
   *C09K 11/06* (2006.01)

(52) U.S. Cl.
   CPC ...... *H01L 51/009* (2013.01); *C09K 2211/188* (2013.01); *H01L 51/506* (2013.01); *Y02E 10/549* (2013.01); *Y02P 70/521* (2015.11)

(58) Field of Classification Search
   CPC ........... H01L 51/0061; H01L 51/00752; H01L 51/0073; H01L 51/5072; C09K 2211/188
   USPC ................ 252/500–519.1, 510, 511, 519.21; 257/40
   See application file for complete search history.

(56) References Cited

U.S. PATENT DOCUMENTS

| | | | |
|---|---|---|---|
| 6,423,429 B2 | 7/2002 | Kido et al. | |
| 6,589,673 B1 | 7/2003 | Kido et al. | |
| 6,891,330 B2 | 5/2005 | Duggal et al. | 313/511 |
| 7,632,703 B2 | 12/2009 | Wu et al. | |
| 8,314,545 B2 | 11/2012 | Tsuji et al. | |
| 8,513,702 B2 | 8/2013 | Schmid et al. | 257/157 |
| 8,734,963 B2 | 5/2014 | De Cola et al. | 428/690 |
| 8,860,009 B2 | 10/2014 | Ueno et al. | 257/40 |
| 2005/0230665 A1* | 10/2005 | Thompson | C09K 11/06 252/500 |
| 2007/0082284 A1* | 4/2007 | Stoessel | C07D 213/26 430/84 |
| 2011/0089408 A1 | 4/2011 | Schmid et al. | 257/40 |
| 2011/0108819 A1* | 5/2011 | Kathirgamanathan | C07D 263/57 257/40 |
| 2013/0200353 A1 | 8/2013 | Schmid et al. | |
| 2015/0123047 A1 | 5/2015 | Maltenberger et al. | 252/519.21 |
| 2015/0162534 A1 | 6/2015 | Maltenberger et al. | 252/519.21 |

FOREIGN PATENT DOCUMENTS

| | | | |
|---|---|---|---|
| EP | 0 510 541 B1 | 12/1995 | |
| EP | 1 220 339 A2 | 7/2002 | |
| EP | 1768200 | 3/2007 | |
| EP | 2276086 | 1/2011 | |
| EP | 1 089 361 B1 | 3/2014 | |
| JP | 0596860 A | 4/1993 | ............ B41M 5/26 |
| JP | b41 m | 4/1993 | ............ B41M 5/30 |
| JP | 1131588 A | 2/1999 | ............ C09K 11/06 |
| JP | 2002-008741 | * 1/2002 | ............ H01M 14/00 |
| JP | 2002-110357 | * 4/2002 | ............ H05B 33/14 |
| JP | 2010530618 A | 9/2010 | ............ H01L 51/50 |
| JP | 2012504569 A | 2/2012 | ............ C07F 15/00 |
| JP | 2015526881 A | 9/2015 | ............ C07C 53/18 |
| KR | 1020040098035 A | 11/2004 | ............ H01L 51/50 |
| KR | 1020110015525 A | 2/2011 | ............ H01L 51/54 |
| KR | 1020150027075 A | 3/2015 | ............ H01L 51/00 |
| WO | 2005/061654 | 7/2005 | |
| WO | 2005/086251 | 9/2005 | |
| WO | 2008/154915 | 12/2008 | |
| WO | 2008/155310 A1 | 12/2008 | |
| WO | 2011/033023 | 3/2011 | |
| WO | 2011/120709 | 10/2011 | |
| WO | 2012/007087 | 1/2012 | |
| WO | PCT/2013/059911 | 5/2013 | |

OTHER PUBLICATIONS

Jun Endo et al., "Organic Electroluminescent Devices with a Vacuum-Deposited Lewis-Acid-Doped Hole-Injecting Layer," Japanese Journal of Applied Physics, vol. 41, Part 2, No. 3B, 2002, 2 pages.

German Office Action for German Priority Patent Application No. 10 2012 209 523.3, dated Feb. 8, 2013, 5 pages.

English Language International Search Report for PCT/EP2013/059911, dated Nov. 22, 2013, 3 pages.

Lewe, T. et al., "Syntheses and Properties of Some New Tris(fluorophenyl)antimony and -bismuth Compounds. Crystal Structure of Tris(2,6-difluorophenyl)bismuth," Zeitschrift fuer anorganische and allgemeine Chemie, vol. 622, No. 12, pp. 2009-2015 (German language w/ English abstract), May 8, 1996.

Sharutin, V. V. et al., "Synthesis and Structure of Triphenyl Bismuth Bis(Fluorobenzoates)," Russian Journal of Coordination Chemistry, vol. 29, No. 7, pp. 462-467, Jul. 15, 2002.

Dikarev, Evgeny V. et al., "Rational Syntheses, Structure, and Properties of the First Bismuth(II) Carboxylate," Inorganic Chemistry, vol. 43, No. 11, pp. 3461-3466, Jan. 14, 2004.

Gielen, Marcel et al., "Di-n-Butyltin and Diethyltin Monofluorobenzoates: Synthesis, Spectroscopic Characterization and In Vitro Antitumor Activity," Applied Organometallic Chemistry, vol. 7, pp. 119-125, Jul. 17, 1992.

Gielen, Marcel et al., "Diorganotin Difluorobenzoates: Synthesis, Spectroscopic Characterization and In VitroAntitumour Activity, X-Ray Structure Determination of bis[di-n-buty1(2,6-difluorobenzoato)time] Oxide," Journal of Fluorine Chemistry, vol. 64, pp. 279-291, Nov. 27, 1992.

Xu, Hao Long et al., "Catalytic Oxidation of Diorganotin(IV) Carboxylates to Mixed-Ligand Monoalkyltin(IV) Carboxylates by $Ag^+$ and Structure Characterization of the Mixed-Ligand Monoalkyltin(IV) 2-Pyridinecarboxylate (2-C/$PhCH_2$)Sn(2-Cl$PhCO_2$)($O_2CC_5H_4$N-2)$_2$," Journal of Organometallic Chemistry, vol. 691, pp. 3331-3335, Mar. 6, 2006.

Shang, Xianmei et al., "Synthesis and Crystal Structure of a Novel Diorganotin(IV) Complex Containing 3,4-Difluorobenzohydroxamato Ligand," Chinese Chemical Letters, vol. 17, No. 6, pp. 821-824, Jun. 2006.

Ma, C. et al., "Drum-Shaped Mono-Organooxotin Assembly Through Solvothermal Synthesis with 2,3,4,5-Tetrafluorobenzoic Acid: Crystal Structure, Hydrogen Bonding and ππ Stacking Interactions," Journal of Coordination Chemistry, vol. 61, No. 2, pp. 211-219, Nov. 1, 2006.

Qui, Lin-Lin et al., "Di-$\mu_3$-oxo-bix($\mu_2$-2,3,4,5-tetrafluoro-benzoato-$\kappa^2$O:O')bis(2,3,4,5-tetrafluoro-benzoato-κO)tetrakis[dimethyltin(IV)]," Acta Crystallographica Section E, Structure Reports, 12 pages, Jun. 25, 2007.

Shang, Xianmei et al., "Mononuclear Diorganotin(IV) Complexes with Arylhydroxamates: Synthesis, Structures and Assessment of In Vitro Cytotoxicity," Applied Organometallic Chemistry, vol. 21, pp. 919-925, Jun. 29, 2007.

Sun, Junsham et al., "Dimethyl(1,10-phenanthroline)-bis(2,3,4,5-tetrafluorobenzoato)tin(IV)" Acta Crystallographica Section E, Structure Reports, 11 Pages, Oct. 2, 2007.

(56) References Cited

OTHER PUBLICATIONS

Liu, Hong et al., Bis(μ-3,5-difluorobenzoato)bis[(3,5-difluorobenzoato)dimethyltin(IV)], Metal-Organic Compounds, Structure Reports, 7 pages, Dec. 24, 2010.

Sharutin, V. V. et al., "Synthesis and Structure of Bismuth Tris(3-Methylbenzoate) [Bi($O_2CC_6H_4CH_3$-3)$_3$]$_\infty$ and Phenylbismuth Bis(3,4,5-Trifluorobenzoate) [PhBi(μ-$O_2CC_6H_2F_3$-3,4,5)($O_2CC_6H_2F_3$-3,4,5)]$_2$," Russian Journal of Coordination Chemistry, vol. 30, No. 5, pp. 309-313, 2004.

Sharutin, V. V. et al, "Synthesis and Structure of Bismuth Tris(3-Methylbenzoate) and Phenylbismuth Bis(3,4,5-Trifluorobenzoate) [PhBi(μ-$O_2CC_6H_2F_3$-3,4,5)($O_2CC_6H_2F_3$-3,4,5)]$_2$," Russian Journal of Coordination Chemistry, vol. 30, No. 5, pp. 309-313, Apr. 30, 2003.

U.S. Non-Final Office Action, U.S. Appl. No. 15/383,579, 21 pages, dated Apr. 16, 2018.

U.S. Final Office Action, U.S. Appl. No. 15/383,579, 9 pages, dated Oct. 5, 2018.

\* cited by examiner

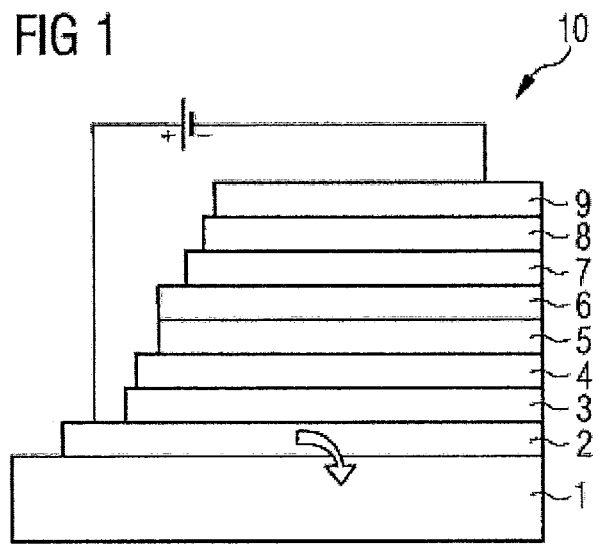
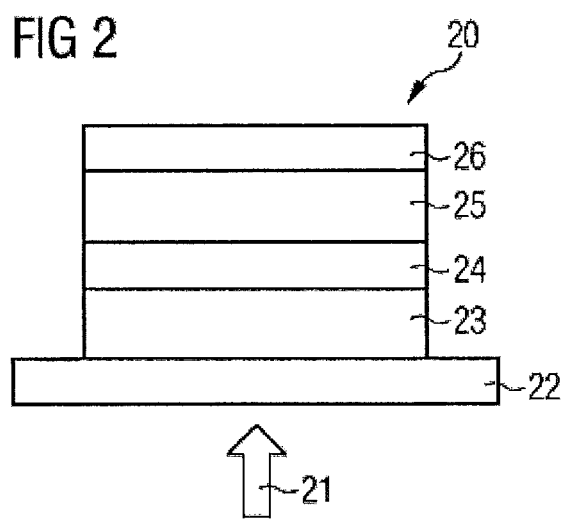
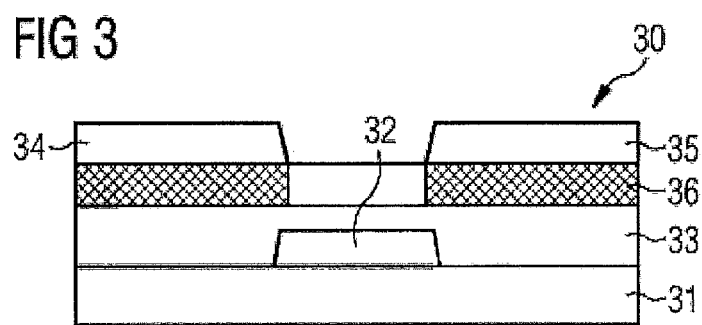

MAIN GROUP METAL COMPLEXES AS P-DOPANTS FOR ORGANIC ELECTRONIC MATRIX MATERIALS

CROSS REFERENCE TO RELATED APPLICATIONS

This application is based on and hereby claims priority to International Application No. PCT/EP2013/059911 filed on May 14, 2013 and German Application No. 10 2012 209 523.3 filed on Jun. 6, 2012, the contents of which are hereby incorporated by reference.

BACKGROUND

Described below is the use of bi- or polynuclear main group metal complexes as p-dopants for organic electronic matrix materials.

Within organic electronics, it is possible to identify essentially two important commercial fields of technology. The first field of technology is concerned with uses of organic matrix materials for conversion of light to electrical current and vice versa, and the other field is focused on the construction of electrical components by organic semiconductor material. Examples of the former category are, for example, photodetectors and organic solar cells, shown in schematic form in FIG. 1, which convert light to an electrical signal or to electrical current, and organic light-emitting diodes (OLEDs), which can generate light by organic electronic materials (see FIG. 2). In the second field of technology are, for example, organic field-effect transistors, shown in schematic form in FIG. 3, in which doping reduces the contact resistance between electrode and semiconductor material, or bipolar transistors.

A common factor to all the applications is that they include, as an important functional component, electrical transport layers which have different conduction mechanisms depending on their composition. In general, a distinction is made between intrinsic p-conductivity (hole conductivity) and n-conductivity (electron conductivity) of the organic materials. Since the electrical properties of these organic substance classes are generally insufficient for high-efficiency utilization of the components, they are admixed with additional compounds which are intended to improve the electrical properties of the layers. This is typically done by doping with metallic or further organic compounds. One approach to achieving significant improvements in conductivities is the addition of metal complexes and especially the addition of transition metal complexes.

For example, WO 2005 086251 describes dopants for production of n-conductive layers which may have structures including the following:

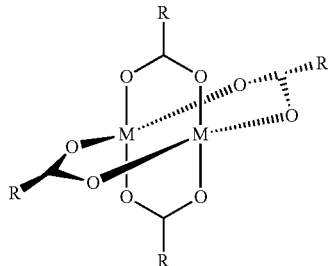

The structure of this compound class is also referred to in the literature as "paddle wheel complex". More particularly, the publication describes the use of a metal complex as n-dopant for doping an organic semiconductive matrix material to alter the electrical properties thereof. The compounds presented are said, with respect to the matrix material, to be usable as n-dopants.

Another way of using Lewis-acidic metal complexes to dope p-conductive transport layers is given by Endo et al. (Jpn. J. Appl. Phys. vol. 41 (2002) L358-L360). This reference describes organic electroluminescent devices having a p-conductive layer which are prepared by co-doping from $FeCl_3$ and arylamine derivatives, for example N,N'-dinaphthyl-N,N-diphenylbenzidine (α-NPD). However, significant disadvantages for the component are also described therein, such as extinguishment of the luminescence and an increase in intrinsic absorption.

A further way of configuring organic semiconductors for bipolar transistors by doping is additionally disclosed in DE 102010041331.

Additionally known are polynuclear metal complexes, for example from WO 2008/154915.

SUMMARY

One possible object is further materials which are suitable as p-dopants in organic electronic matrix materials, especially hole transporters, and increase the efficiency of components containing these layers.

The inventors propose an organic electronic component having a matrix is proposed, wherein the matrix contains, as p-dopant, a main group metal complex of groups 13 to 15 which in turn contains at least one ligand L of the following structure:

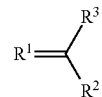

where $R^1$ and $R^2$ are each independently oxygen, sulfur, selenium, NH or $NR^4$ where $R^4$ is selected from the group comprising alkyl and aryl and may be bonded to $R^3$; and $R^3$ is selected from the group comprising alkyl, long-chain alkyl, alkoxy, long-chain alkoxy, cycloalkyl, haloalkyl, aryl, arylenes, haloaryl, heteroaryl, heteroarylenes, heterocycloalkylenes, heterocycloalkyl, haloheteroaryl, alkenyl, haloalkenyl, alkynyl, haloalkynyl, ketoaryl, haloketoaryl, ketoheteroaryl, ketoalkyl, haloketoalkyl, ketoalkenyl, haloketoalkenyl, where one or more non-adjacent $CH_2$ groups in suitable radicals may independently be replaced by —O—, —S—, —NH—, —NR°—, —SiR°R°°—, —CO—, —COO—, —OCO—, —OCO—O—, —SO$_2$—, —S—CO—, —CO—S—, —CY1=CY2— or —C≡C—, in such a way that no oxygen and/or sulfur atoms are bonded directly to one another, and are likewise optionally replaced by aryl or heteroaryl preferably containing 1 to 30 carbon atoms (terminal $CH_3$ groups are regarded as $CH_2$ groups in the sense of $CH_2$—H).

It has been found that, surprisingly, these materials are suitable as p-dopants for matrix materials in organic electronic components. More particularly, these materials often have one or more of the following advantages:

The materials have good co-evaporability together with the matrix material from various sources, such that doped matrix layers of defined composition form.

The materials are obtainable in a simple way and do not require any complex preparation processes.

The doping strength can be adapted to the matrix.

The conductivity can be adjusted via the concentration and type of substance.

In the context of this discussion, the term "organic electronic component" means and/or encompasses especially organic transistors, organic light-emitting diodes, light-emitting electrochemical cells, organic solar cells, photodiodes and organic photovoltaics in general.

In the context of this discussion, the term "p-dopant" means or encompasses especially materials which have Lewis acidity and/or are capable of forming complexes with the matrix material in which these materials act as Lewis acids (if only in a formal sense).

Such a main group metal complex matrix material (hole conductor) may have, for example, the following structure (shown here with bismuth as metal and coordination via the nitrogen):

The term "main group metal complex of groups 13 to 15" is understood to mean the metals of groups 13 to 15 according to IUPAC, i.e. aluminum, gallium, indium, silicon, germanium, tin, lead, thallium, arsenic, antimony, bismuth or mixtures thereof. Preference is given to the metals of groups 14 and 15, i.e. silicon, germanium, tin, lead, arsenic, antimony, bismuth, more preferably tin and/or bismuth.

General group definitions: general groups, for example alkyl, alkoxy, aryl etc., are described. Unless stated otherwise, preference is given in the context of these documents to using the groups which follow within the groups described in general terms:

alkyl: linear and branched C1-C8-alkyls,
long-chain alkyls: linear and branched C5-C20 alkyls
alkenyl: C2-C6-alkenyl, cycloalkyl: C3-C8-cycloalkyl,
alkoxy: C1-C6-alkoxy,
long-chain alkoxy: linear and branched C5-C20 alkoxy
alkylene: selected from the group comprising: methylene; 1,1-ethylene; 1,2-ethylene; 1,1-propylidene; 1,2-propylene; 1,3-propylene; 2,2-propylidene; butan-2-ol-1,4-diyl; propan-2-ol-1,3-diyl; 1,4-butylene; cyclohexane-1,1-diyl; cyclohexane-1,2-diyl; cyclohexane-1,3-diyl; cyclohexane-1,4-diyl; cyclopentane-1,1-diyl; cyclopentane-1,2-diyl; and cyclopentane-1,3-diyl,
aryl: selected from aromatics having a molecular weight below 300 Da.
arylene: selected from the group comprising: 1,2-phenylene; 1,3-phenylene; 1,4-phenylene; 1,2-naphthylene; 1,3-naphthalenylene; 1,4-naphthylene; 2,3-naphthylene; 1-hydroxy-2,3-phenylene; 1-hydroxy-2,4-phenylene; 1-hydroxy-2,5-phenylene; and 1-hydroxy-2,6-phenylene,
heteroaryl: selected from the group comprising: pyridinyl; pyrimidinyl; pyrazinyl; triazolyl; pyridazinyl; 1,3,5-triazinyl; quinoninyl; isoquinoninyl; quinoxalinyl; imidazolyl; pyrazolyl; benzimidazolyl; thiazolyl; oxazolidinyl; pyrrolyl; thiophenyl; carbazolyl; indolyl; and isoindolyl, where the heteroaryl may be bonded to the compound via any atom in the ring of the selected heteroaryl.
heteroarylene: selected from the group comprising: pyridinediyl; quinolinediyl; pyrazodiyl; pyrazolediyl; triazolediyl; pyrazinediyl; thiophenediyl; and imidazolediyl, where the heteroarylene functions as a bridge in the compound via any atom in the ring of the selected heteroaryl, the following being especially preferred: pyridine-2,3-diyl; pyridine-2,4-diyl; pyridine-2,5-diyl; pyridine-2,6-diyl; pyridine-3,4-diyl; pyridine-3,5-diyl; quinoline-2,3-diyl; quinoline-2,4-diyl; quinoline-2,8-diyl; isoquinoline-1,3-diyl; isoquinoline-1,4-diyl; pyrazole-1,3-diyl; pyrazole-3,5-diyl; triazole-3,5-diyl; triazole-1,3-diyl; pyrazine-2,5-diyl; and imidazole-2,4-diyl, thiophene-2,5-diyl, thiophene-3,5-diyl; a —C1-C6-heterocycloalkyl selected from the group comprising: piperidinyl; piperidine; 1,4-piperazine, tetrahydrothiophene; tetrahydrofuran; 1,4,7-triazacyclononane; 1,4,8,11-tetraazacyclotetradecane; 1,4,7,10,13-pentaazacyclopentadecane; 1,4-diaza-7-thiacyclononane; 1,4-diaza-7-oxacyclononane; 1,4,7,10-tetraazacyclododecane; 1,4-dioxane; 1,4,7-trithiacyclononane; pyrrolidine; and tetrahydropyran, where the heteroaryl may be bonded to the C1-C6-alkyl via any atom in the ring of the selected heteroaryl.
heterocycloalkylene: selected from the group comprising: piperidin-1,2-ylene; piperidin-2,6-ylene; piperidin-4,4-ylidene; 1,4-piperazin-1,4-ylene; 1,4-piperazin-2,3-ylene; 1,4-piperazin-2,5-ylene; 1,4-piperazin-2,6-ylene; 1,4-piperazin-1,2-ylene; 1,4-piperazin-1,3-ylene; 1,4-piperazin-1,4-ylene; tetrahydrothiophen-2,5-ylene; tetrahydrothiophen-3,4-ylene; tetrahydrothiophen-2,3-ylene; tetrahydrofuran-2,5-ylene; tetrahydrofuran-3,4-ylene; tetrahydrofuran-2,3-ylene; pyrrolidin-2,5-ylene; pyrrolidin-3,4-ylene; pyrrolidin-2,3-ylene; pyrrolidin-1,2-ylene; pyrrolidin-1,3-ylene; pyrrolidin-2,2-ylidene; 1,4,7-triazacyclonon-1,4-ylene; 1,4,7-triazacyclonon-2,3-ylene; 1,4,7-triazacyclonon-2,9-ylene; 1,4,7-triazacyclonon-3,8-ylene; 1,4,7-triazacyclonon-2,2-ylidene; 1,4,8,11-tetraazacyclotetradec-1,4-ylene; 1,4,8,11-tetraazacyclotetradec-1,8-ylene; 1,4,8,11-tetraazacyclotetradec-2,3-ylene; 1,4,8,11-tetraazacyclotetradec-2,5-ylene; 1,4,8,11-tetraazacyclotetradec-1,2-ylene; 1,4,8,11-tetraaza-cyclotetradec-2,2-ylidene; 1,4,7,10-tetraazacyclododec-1,4-ylene; 1,4,7,10-tetraazacyclododec-1,7-ylene; 1,4,7,10-tetraazacyclododec-1,2-ylene; 1,4,7,10-tetraazacyclododec-2,3-ylene; 1,4,7,10-tetraazacyclododec-2,2-ylidene; 1,4,7,10,13-pentaazacyclopentadec-1,4-ylene; 1,4,7,10,13-pentaazacyclopentadec-1,7-ylene; 1,4,7,10,13-pentaazacyclopentadec-2,3-ylene; 1,4,7,10,13-pentaazacyclo-pentadec-1,2-ylene; 1,4,7,10,13-pentaazacyclopentadec-2,2-ylidene; 1,4-diaza-7-thiacyclonon-1,4-ylene; 1,4-diaza-7-thia-cyclonon-1,2-ylene; 1,4-diaza-7-thiacyclonon-2,3-ylene; 1,4-diaza-7-thiacyclonon-6,8-ylene; 1,4-diaza-7-thiacyclonon-2,2-ylidene; 1,4-diaza-7-oxacyclonon-1,4-ylene; 1,4-diaza-7-oxa-cyclonon-1,2-ylene; 1,4-diaza-7-oxacyclonon-2,3-ylene; 1,4-diaza-7-oxacyclonon-6,8-ylene; 1,4-diaza-7-oxacyclonon-2,2-ylidene; 1,4-dioxan-2,3-ylene; 1,4-dioxan-2,6-ylene; 1,4-dioxan-2,2-ylidene; tetrahydropyran-2,3-ylene; tetrahydropyran-2,6-ylene; tetra-hydropyran-2,5-ylene; tetrahydropyran-2,2-ylidene; 1,4,7-trithiacyclonon-2,3-ylene; 1,4,7-trithia-cyclonon-2,9-ylene; and 1,4,7-trithiacyclonon-2,2-ylidene,
heterocycloalkyl: selected from the group comprising: pyrrolinyl; pyrrolidinyl; morpholinyl; piperidinyl; piperazinyl;

hexamethyleneimine; 1,4-piperazinyl; tetrahydrothiophenyl; tetrahydrofuranyl; 1,4,7-triazacyclononanyl; 1,4,8,11-tetraazacyclotetradecanyl; 1,4,7,10,13-pentaazacyclopentadecanyl; 1,4-diaza-7-thiacyclo-nonanyl; 1,4-diaza-7-oxacyclononanyl; 1,4,7,10-tetraazacyclododecanyl; 1,4-dioxanyl; 1,4,7-trithiacyclo-nonanyl; tetrahydropyranyl; and oxazolidinyl, where the heterocycloalkyl may be bonded to the compound via any atom in the ring of the selected heterocycloalkyl.

amine: the —N(R)2 group where each R is selected independently from: hydrogen; C1-C6-alkyl; C1-C6-alkyl-C6H5; and phenyl, where, when both R' are C1-C6 alkyl, the two R' may form an —NC3 to NC5 heterocyclic ring, where the rest of the alkyl chain forms an alkyl substituent on the heterocyclic ring halogen: selected from the group comprising: F; Cl; Br and I haloalkyl: selected from the group comprising mono-, di-, tri-, poly- and perhalogenated linear and branched C1-C8-alkyl, more preferably —CF$_3$ pseudohalogen: selected from the group comprising —CN, —SCN, —OCN, N3, —CNO, —SeCN carboxylate: the —C(O)OR group where R is selected from: hydrogen; C1-C6-alkyl; phenyl; C1-C6-alkyl-C6H5;

carbonyl: the —C(O)R group where R is selected from: hydrogen; C1-C6-alkyl; phenyl; C1-C6-alkyl-C6H5 and amines selected from the group of: —NR'2 where each R' is independently selected from: hydrogen; C1-C6-alkyl; C1-C6-alkyl-C6H5; and phenyl, where, when both R' are C1-C6 alkyl, the two R' may form an —NC3 to NC5 heterocyclic ring, where the rest of the alkyl chain forms an alkyl substituent on the heterocyclic ring.

Unless stated otherwise, the following groups are more preferred groups within the general group definitions:

alkyl: linear and branched C1-C6-alkyl, long-chain alkyls: linear and branched C5-C10 alkyl, preferably C6-C8 alkyls alkenyl: C3-C6-alkenyl, cycloalkyl: C6-C8-cycloalkyl, alkoxy: C1-C4-alkoxy, long-chain alkoxy: linear and branched C5-C10 alkoxy, preferably linear C6-C8 alkoxy alkylene: selected from the group comprising: methylene; 1,2-ethylene; 1,3-propylene; butan-2-ol-1,4-diyl; 1,4-butylene; cyclohexane-1,1-diyl; cyclohexane-1,2-diyl; cyclohexane-1,4-diyl; cyclopentane-1,1-diyl; and cyclopentane-1,2-diyl, aryl: selected from the group comprising: phenyl; biphenyl; naphthalenyl; anthracenyl; and phenanthrenyl, arylene: selected from the group comprising: 1,2-phenylene; 1,3-phenylene; 1,4-phenylene; 1,2-naphthylene; 1,4-naphthalenylene; 2,3-naphthylene and 1-hydroxy-2,6-phenylene, heteroaryl: selected from the group comprising: pyridinyl; pyrimidinyl; quinoninyl; pyrazolyl; triazolyl; isoquinoninyl; imidazolyl; and oxazolidinyl, where the heteroaryl may be bonded to the compound by any atom in the ring of the selected heteroaryl, heteroarylene: selected from the group comprising: pyridine-2,3-diyl; pyridine-2,4-diyl; pyridine-2,6-diyl; pyridine-3,5-diyl; quinoline-2,3-diyl; quinoline-2,4-diyl; isoquinoline-1,3-diyl; isoquinoline-1,4-diyl; pyrazole-3,5-diyl; and imidazole-2,4-diyl, heterocycloalkyl: selected from the group comprising: pyrrolidinyl; morpholinyl; piperidinyl; piperidinyl; 1,4-piperazinyl; tetrahydrofuranyl; 1,4,7-triazacyclononanyl; 1,4,8,11-tetraazacyclotetradecanyl; 1,4,7,10,13-pentaazacyclopentadecanyl; 1,4,7,10-tetraazacyclododecanyl; and piperazinyl, where the heteroaryl may be bonded to the compound by any atom in the ring of the selected heteroaryl heterocycloalkylene: selected from the group comprising: piperidin-2,6-ylene; piperidin-4,4-ylidene; 1,4-piperazin-1,4-ylene; 1,4-piperazin-2,3-ylene; 1,4-piperazin-2,6-ylene; tetrahydrothiophen-2,5-ylene; tetrahydrothiophen-3,4-ylene; tetrahydrofuran-2,5-ylene; tetrahydrofuran-3,4-ylene; pyrro-lidin-2,5-ylene; pyrrolidin-2,2-ylidene; 1,4,7-triazacyclonon-1,4-ylene; 1,4,7-triazacyclonon-2,3-ylene; 1,4,7-triazacyclonon-2,2-ylidene; 1,4,8,11-tetraazacyclotetradec-1,4-ylene; 1,4,8,11-tetraazacyclotetradec-1,8-ylene; 1,4,8,11-tetraazacyclotetradec-2,3-ylene; 1,4,8,11-tetraazacyclotetra-dec-2,2-ylidene; 1,4,7,10-tetraazacyclododec-1,4-ylene; 1,4,7,10-tetraazacyclododec-1,7-ylene; 1,4,7,10-tetraazacyclo-dodec-2,3-ylene, 1,4,7,10-tetraazacyclododec-2,2-ylidene; 1,4,7,10,13-pentaazacyclopentadec-1,4-ylene; 1,4,7,10,13-pentaazacyclopentadec-1,7-ylene; 1,4-diaza-7-thiacyclonon-1,4-ylene; 1,4-diaza-7-thiacyclonon-2,3-ylene; 1,4-diaza-7-thiacyclonon-2,2-ylidene; 1,4-diaza-7-oxacyclonon-1,4-ylene; 1,4-diaza-7-oxacyclonon-2,3-ylene; 1,4-diaza-7-oxacyclonon-2,2-ylidene; 1,4-dioxan-2,6-ylene; 1,4-dioxan-2,2-ylidene; tetrahydropyran-2,6-ylene; tetrahydropyran-2,5-ylene; and tetrahydropyran-2,2-ylidene, a —C1-C6-alkylheterocycloalkyl where the heterocycloalkyl is selected from the group comprising: piperidinyl; 1,4-piperazinyl; tetrahydrofuranyl; 1,4,7-triazacyclononanyl; 1,4,8,11-tetraazacyclotetradecanyl; 1,4,7,10,13-pentaazacyclopentadecanyl; 1,4,7,10-tetraazacyclo-dodecanyl; and pyrrolidinyl, where the heterocycloalkyl may be bonded to the compound by any atom in the ring of the selected heterocycloalkyl amine: the —N(R)2 group where each R is independently selected from: hydrogen; C1-C6-alkyl; and benzyl, halogen: selected from the group comprising: F and Cl, carboxylate: the —C(O)OR group where R is selected from hydrogen; C1-C6-alkyl; and benzyl, carbonyl: the —C(O)R group where R is selected from: hydrogen; C1-C6-alkyl; benzyl and amines selected from the group of: —NR'2 where each R' is independently selected from:

hydrogen; C1-C6-alkyl; and benzyl.

In a preferred embodiment, $R^3$ is haloalkyl, more preferably perfluoroalkyl having 1 to 8 carbons, more preferably 1 to 4, haloaryl, more preferably perfluoroaryl, haloalkylaryl, especially preferably (per)fluoroalkylaryl and halohetereoaryl, especially preferably perfluoroheteroaryl.

Further examples of ligands L preferably include fluorinated benzoic acids, for example 2-(trifluoromethyl)benzoic acid; 3,5-difluorobenzoic acid; 3-hydroxy-2,4,6-triiodobenzoic acid; 3-fluoro-4-methylbenzoic acid; 3-(trifluoromethoxy)benzoic acid; 4-(trifluoromethoxy)-benzoic acid; 4-chloro-2,5-difluorobenzoic acid; 2-chloro-4,5-difluorobenzoic acid; 2,4,5-trifluorobenzoic acid; 2-fluorobenzoic acid; 4-fluorobenzoic acid; 2,3,4-trifluorobenzoic acid; 2,3,5-trifluorobenzoic acid; 2,3-difluorobenzoic acid; 2,4-bis(trifluoromethyl)benzoic acid; 2,4-difluorobenzoic acid; 2,5-difluorobenzoic acid; 2,6-bis(trifluoromethyl)benzoic acid; 2,6-difluorobenzoic acid; 2-chloro-6-fluorobenzoic acid; 2-fluoro-4-(trifluoromethyl)-benzoic acid; 2-fluoro-5-(trifluoromethyl)benzoic acid; 2-fluoro-6-(trifluoromethyl)benzoic acid; 3,4,5-trifluorobenzoic acid; 3,4-difluorobenzoic acid; 3,5-bis(trifluoromethyl)benzoic acid; 3-(trifluoromethyl)benzoic acid; 3-chloro-4-fluorobenzoic acid; 3-fluoro-5-(trifluoromethyl)benzoic acid; 3-fluorobenzoic acid; 4-fluoro-2-(trifluoromethyl)benzoic acid; 4-fluoro-3-(trifluoromethyl)benzoic acid; 5-fluoro-2-methylbenzoic acid;

2-(trifluoromethoxy)benzoic acid; 2,3,5-trichlorobenzoic acid; 4-(trifluoromethyl)benzoic acid; pentafluorobenzoic acid; 2,3,4,5-tetrafluorobenzoic acid, fluorinated or non-fluorinated phenylacetic acid, for example 2-fluorophenylacetic acid; 3-fluorophenylacetic acid; 4-fluorophenylacetic acid; 2,3-difluorophenylacetic acid; 2,4-difluorophenylacetic acid; 2,6-difluorophenylacetic acid; 3,4-difluorophenylacetic acid; 3,5-difluorophenylacetic acid; pentafluoro-phenylacetic acid; 2-chloro-6-fluorophenylacetic acid; 2-chloro-3,6-difluorophenylacetic acid; 3-chloro-2,6-difluoro-phenylacetic acid; 3-chloro-4-fluorophenylacetic acid; 5-chloro-2-fluorophenylacetic acid; 2,3,4-trifluorophenylacetic acid; 2,3,5-trifluorophenylacetic acid; 2,3,6-trifluoro-phenylacetic acid; 2,4,5-trifluorophenylacetic acid; 2,4,6-trifluorophenylacetic acid; 3,4,5-trifluorophenylacetic acid; 3-chloro-2-fluorophenylacetic acid; α-fluorophenylacetic acid; 4-chloro-2-fluorophenylacetic acid; 2-chloro-4-fluorophenyl-acetic acid; α,α-difluorophenylacetic acid; ethyl 2,2-difluoro-2-phenylacetate; and fluorinated or non-fluorinated acetic acid, for example methyl trifluoroacetate; allyl trifluoroacetate; ethyl trifluoroacetate; isopropyl trifluoroacetate; 2,2,2-trifluoroethyl trifluoroacetate; difluoroacetic acid; trifluoroacetic acid; methyl chlorodifluoroacetate; ethyl bromodifluoroacetate; chlorodifluoroacetic acid; ethyl chlorofluoroacetate; ethyl difluoroacetate; (3-chlorophenyl)-difluoroacetic acid; (3,5-difluorophenyl)difluoroacetic acid; (4-butylphenyl)difluoroacetic acid; (4-tert-butylphenyl)-difluoroacetic acid; (3,4-dimethylphenyl)difluoroacetic acid; (3-chloro-4-fluorophenyl)difluoroacetic acid; (4-chlorophenyl)-difluoroacetic acid; 2-biphenyl-3',5'-difluoroacetic acid; 3-biphenyl-3',5'-difluoroacetic acid; 4-biphenyl-3',5'-difluoroacetic acid; 2-biphenyl-3',4'- difluoroacetic acid; 3-biphenyl-3',4'-difluoroacetic acid; 4-biphenyl-3',4'-difluoroacetic acid and 2,2-difluoropropionic acid, or higher homologs thereof. If the ligands L have acidic groups, the groups may, in a preferred embodiment, be in deprotonated form.

In an alternative preferred embodiment, $R^3$ is selected from the group comprising:

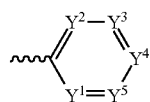

where $Y^1$-$Y^5$ are each independently selected from the group comprising C—F, C—CF$_3$, C—NO$_2$, C—CN, C-halogen, C-pseudohalogen and N.

In a preferred embodiment, $R^3$ is selected from the group comprising:

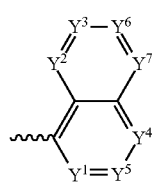

where $Y^1$-$Y^7$ are each independently selected from the group comprising C—F, C—CF$_3$, C—NO$_2$, C—CN, C-halogen, C-pseudohalogen and N.

In a preferred embodiment, $R^3$ is selected from the group comprising:

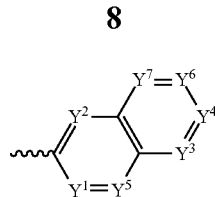

where $Y^1$-$Y^7$ are each independently selected from the group comprising C—F, CF$_3$, C—NO$_2$, C—CN, C-halogen, C-pseudohalogen and N.

In a preferred embodiment, $R^3$ is selected from the group comprising:

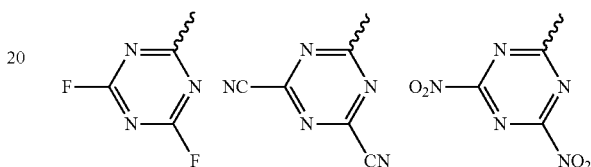

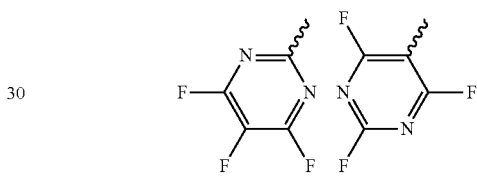

In a preferred embodiment, $R^3$ is selected from the group comprising halogenated, preferably perhalogenated and/or pseudohalogenated, pteridines, isopteridines, naphthyridines, quinoxalines, azaquinoxalines.

In a preferred embodiment, the metal complex (in the absence of matrix material) is Lewis-acidic, meaning that it acts as an electron pair acceptor. This has been found to be particularly preferred for interaction with the matrix materials.

In a preferred embodiment, the metal complex (in the absence of matrix material) has at least one unoccupied or partly accessible coordination site. This has likewise been found to be particularly preferred for interaction with the matrix materials.

In a preferred embodiment, the compounds can be processed either in the gas phase or in the liquid phase. In the case of gas phase deposition, both dopant and matrix material are co-vaporized under high vacuum, preferably from different sources, and deposited as a layer. In the case of processing from the liquid phase, the metal complex and the matrix material are dissolved in a solvent and deposited by printing techniques, spin-coating, knife-coating, slot-coating, etc. The finished layer is obtained by vaporizing the solvent. It is possible to establish any desired doping ratios via the different mass ratios of metal complex to the matrix material.

It is possible with particular preference to process the following hole conductors by a solvent process:

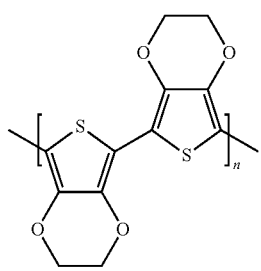

PDOT =
poly(3,4-ethylenedioxythio-phene)

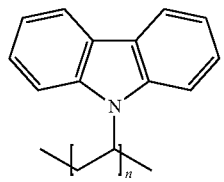

PVK =
poly(9-vinylcarbazole)

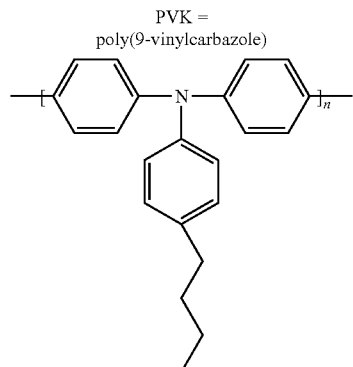

PTPD =
poly(N,N'-bis(4-butylphenyl)-N,N'-
bis(phenyl)benzidine)

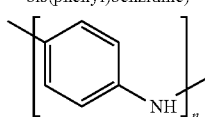

PANI =
polyaniline

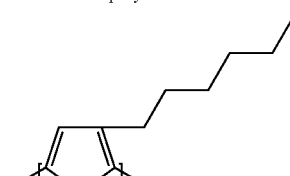

P3HT =
poly(3-hexylthiophene)

In addition, it is possible by a solvent process, with particular preference, to process matrix materials which are referred to as "small molecules". This substance class is known to those skilled in the art and includes, for example, spiro-TAD (2,2',7,7'-tetrakis(N,N-diphenylamino)-9,9'-spirobi-fluorene) and spiro-TTB (2,2',7,7'-tetrakis(N,N'-di-p-methyl-phenylamino)-9,9'-spirobifluorene), and further materials as listed as matrix materials in this application.

In a preferred embodiment, the metal complex is a mono- or bi- or polynuclear metal complex. More particularly, the metal complex may be in solid form as a polynuclear metal complex. The polynuclear metal complex in solid form may depolymerize during vaporization and may advantageously be in mononuclear form in the gas phase. This embodiment is particularly advantageous since particularly intimate mixing and good binding of the complexes to the matrix materials are thus effected.

In a preferred embodiment, at least one of the ligands L is in a bridging arrangement between two metals.

In a preferred embodiment, the metal complex has the empirical formula $M_2L_4$ (with M =metal and L=ligand) where both the metals and the individual ligands may independently be selected as defined above.

In a further preferred embodiment, the metal complex may contain the metal atom M as Sn, Sb, Pb or bismuth. More preferably, the metal complexes may either be mononuclear according to the structures given below

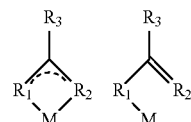

or be dinuclear according to the structures given below:

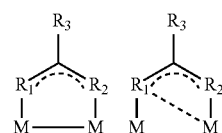

Without being bound to the theory, there is terminal coordination of the metal via the ligand(s) in the mononuclear complexes. In the case of a dinuclear complex, there is bi- or tridentate coordination of the metal atom. If different metal atoms are employed to form a bidentate complex, a hetero-bimetallic complex is the result.

More preferably, the main group metal complex contains bismuth. In this context, particular preference is given to bismuth main group metal complexes:

The II oxidation states which, without being bound to the theory, as a function of the ligands chosen, may have the following paddle-wheel structure:

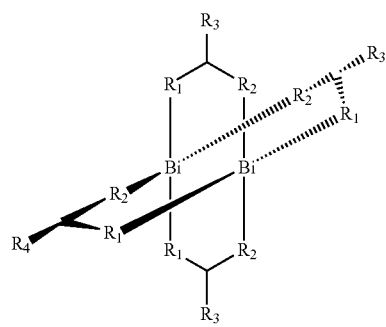

The III oxidation state ($ML_n=3$) which, without being bound to the theory, does not have a paddle-wheel structure.

These compounds are generally in solid form in mono- or polynuclear form, and can depolymerize during the vaporization process.

The V oxidation state, in which, in a particular embodiment, the main group metal complex may contain bismuth in the V oxidation state with the following structure:

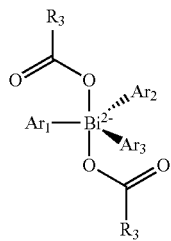

The $Ar_i$ may, in this preferred case, independently be selected from the group of the substituted or unsubstituted aromatics or heteroaromatics. A particular embodiment involves partially fluorinated or perfluorinated aromatics or heteroaromatics. In addition, the $Ar_i$ may more preferably be selected from the group of the non-fluorinated or fluorinated carboxylates or generally from the group of ligands L as listed in this application.

In an alternative embodiment, the metal complex has the structure $ML_m$ with M=metal, L=ligand and m=1 to 10, where, when m>1, all L are independent of one another. These metal complexes are preferred, especially in the case of tin and bismuth; in this case, m is preferably m=2 for tin, or 2, 4, and 3 or 5 for bismuth, according to the oxidation state.

In an alternative embodiment, the metal complex has the structure $ML_2L'_n$ with M=metal, L=ligand, as defined above, and L'=a ligand nonidentical to L, selected from the group of aryl, heteroaryl, haloaryl and haloheteroaryl, where n may be from 0 to 3 and, if n>1, each L' is selected independently from the others. These metal complexes are preferred especially in the case of tin and bismuth; in this case, preferably, n=2 for tin, or 1 or 3 for bismuth, according to the oxidation state, and n=0.

In a preferred embodiment, the matrix material of the optoelectronic component comprises one or more of the following materials:
NPB (N,N'-bis(naphthalen-1-yl)-N,N'-bis(phenyl)benzidine)
β-NPB (N,N'-bis(naphthalen-2-yl)-N,N'-bis(phenyl)benzidine)
TPD (N,N'-bis(3-methylphenyl)-N,N'-bis(phenyl)benzidine)
spiro-TPD (N,N'-bis(3-methylphenyl)-N,N'-bis(phenyl)benzidine)
spiro-NPB (N,N'-bis(naphthalen-1-yl)-N,N'-bis(phenyl)spiro)
DMFL-TPD (N,N'-bis(3-methylphenyl)-N,N'-bis(phenyl)-9,9-dimethylfluorene)
DMFL-NPB (N,N'-bis(naphthalen-1-yl)-N, N'-bis(phenyl)-9,9-dimethylfluorene)
DPFL-TPD (N,N'-bis(3-methylphenyl)-N,N'-bis(phenyl)-9,9-diphenylfluorene)
DPFL-NPB (N,N'-bis(naphthalen-1-yl)-N,N'-bis(phenyl)-9,9-diphenylfluorene)
spiro-TAD (2,2',7,7'-tetrakis(N,N-diphenylamino)-9,9'-spirobi-fluorene)
9,9-bis[4-(N, N-bis(biphenyl-4-yl)amino)phenyl]-9H-fluorene
9,9-bis[4-(N,N-bis(naphthalen-2-yl)amino)phenyl]-9H-fluorene
9,9-bis[4-(N, N'-bis(naphthalen-2-yl)-N,N'-bisphenylamino)-phenyl]-9H-fluorene
N,N'-bis(phenanthren-9-yl)-N, N'-bis(phenyl)benzidine
2,7-bis[N, N-bis(9,9-spiro-bifluoren-2-yl)amino]-9,9-spirobifluorene
2,2'-bis[N,N-bis(biphenyl-4-yl)amino]-9,9-spirobifluorene
2,2'-bis(N,N-diphenylamino)-9,9-spirobifluorene
di[4-(N, N-ditolylamino)phenyl]cyclohexane
2,2',7,7'-tetra(N,N-ditolylamino)spirobifluorene
N, N, N',N'-tetranaphthalen-2-ylbenzidine
spiro-TTB (2,2',7,7'-tetrakis(N,N'-di-p-methylphenylamino)-9,9'-spirobifluorene).

These materials have been found to be useful as matrix materials in (opto)electronic components.

In a preferred embodiment, the doping level in mol of metal complex based on mol of matrix material is from ≥0.1% to ≤50%. This has been found to be appropriate to the purpose. Preferably, the doping level is from ≥0.5% to ≤15%, more preferably ≥1% to ≤5%.

In a preferred embodiment, R3 is selected from the group comprising halogenated, preferably perhalogenated and/or pseudohalogenated, pteridines, isopteridines, naphthyridines, quinoxalines, azaquinoxalines.

In a further preferred embodiment, the metal complex may contain at least one ligand L selected from the group of the unsubstituted, partly fluorinated or perfluorinated organic carboxylic acids. Organic carboxylic acids may generally be selected from the groups of the aliphatically, saturated monocarboxylic acids; aliphatically, unsaturated monocarboxylic acids; aliphatically, saturated dicarboxylic acids; aliphatically, saturated tricarboxylic acids; aliphatically, unsaturated dicarboxylic acids; aromatic carboxylic acids; heterocyclic carboxylic acids; aliphatically, unsaturated cyclic monocarboxylic acids. Particularly preferred partial or perfluorinated ligands L are selected from substituted and unsubstituted compounds of acetic acid, phenylacetic acid and/or benzoic acid, and are listed by way of example above. Particular preference is given to non-fluorinated, partially fluorinated or perfluorinated acetic acid. In a further preferred embodiment, there may be one or more polydentate bridging ligands L between the metal atoms of the complex.

The inventor also propose the use of a group 13-15 metal complex containing at least one ligand L of the following structure:

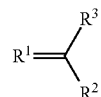

where $R^1$ and $R^2$ are each independently oxygen, sulfur, selenium, NH or $NR^4$ where $R^4$ is selected from the group comprising alkyl and aryl and may be bonded to $R^3$; and $R^3$ is selected from the group comprising alkyl, long-chain alkyl, alkoxy, long-chain alkoxy, cycloalkyl, haloalkyl, aryl, arylenes, haloaryl, heteroaryl, heteroarylenes, heterocycloalkylenes, heterocycloalkyl, haloheteroaryl, alkenyl, haloalkenyl, alkynyl, haloalkynyl, ketoaryl, haloketoaryl, ketoheteroaryl, ketoalkyl, haloketoalkyl, ketoalkenyl, haloketoalkenyl, where one or more non-adjacent $CH_2$ groups in suitable radicals may independently be replaced by —O—, —S—, —NH—, —NR°—, —SiR°R°°—, —CO—, —COO—, —SO$_2$—, —S—CO—, —CO—S—, —CY1=CY2 or —C≡O—, in such a way that no oxygen and/or sulfur atoms are bonded directly to one another, and are likewise optionally replaced by aryl or heteroaryl preferably containing 1 to 30 carbon atoms (terminal CH$_3$ groups are regarded as CH$_2$ groups in the sense of CH$_2$—H), as a p-dopant for matrix materials of electronic components.

The aforementioned components for use with the proposals, and also those described in the working examples, are not subject to any particular exceptional conditions in terms of their size, configuration, materials selection and technical design, and so the selection criteria known in the field of use can be applied without limitation.

BRIEF DESCRIPTION OF THE DRAWINGS

These and other objects and advantages of the present invention will become more apparent and more readily appreciated from the following description of the preferred embodiments, taken in conjunction with the accompanying drawings of which:

FIG. 1 is a schematic side view of the structure of an organic light-emitting diode (10). The light-emitting diode is formed from a glass layer (1); transparent conductive oxide (TCO) or PEDOT:PSS or PANI layer (2); hole injector layer (3); hole transport layer (HTL) (4); emitter layer (EML) (5); hole blocker layer (HBL) (6); electron transport layer (ETL) (7); electron injector layer (8) and a cathode layer (9);

FIG. 2 is a schematic side view of the structure of an organic solar cell having PIN structure (20), which converts light (21) to electrical current. The solar cell is formed of a layer of indium tin oxide (22); a p-doped layer (23); an absorption layer (24); an n-doped layer (25) and a metal layer (26);

FIG. 3 is a schematic cross section of an organic field-effect transistor (30). Atop a substrate (31) is applied a gate electrode (32), a gate dielectric (33), a source and drain contact (34+35) and an organic semiconductor (36). The hatched areas show the points where contact doping is helpful.

DETAILED DESCRIPTION OF THE PREFERRED EMBODIMENT

Figure 4:
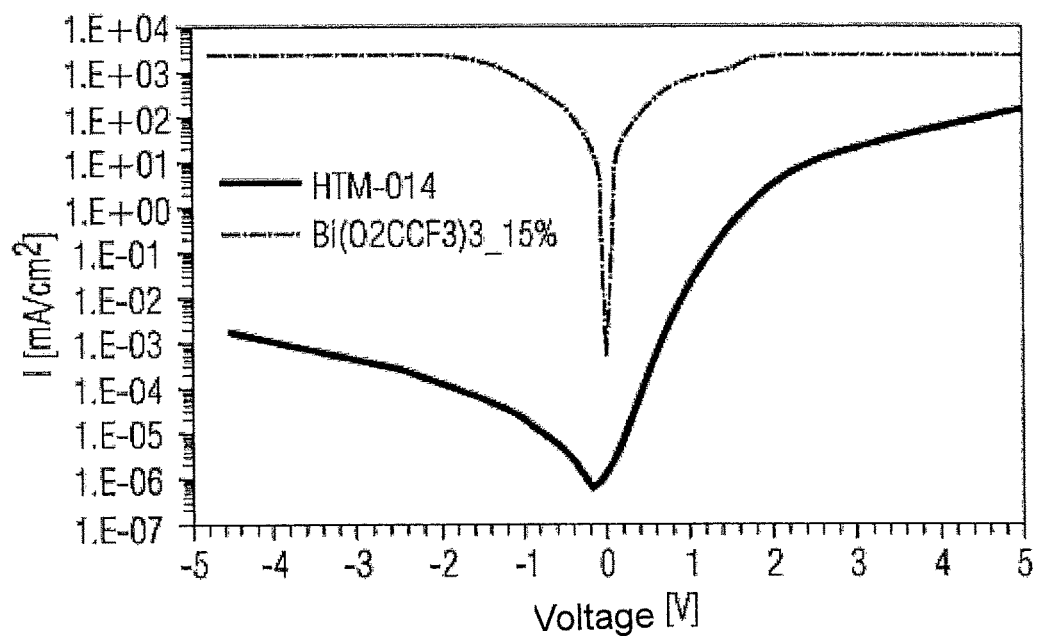
FIG. 4 is a graph of current density against voltage for an undoped matrix material and for a doped matrix material in a first embodiment.

Reference will now be made in detail to the preferred embodiments of the present invention, examples of which are illustrated in the accompanying drawings, wherein like reference numerals refer to like elements throughout.

Example I

Example I relates to Bi(O$_2$CCF$_3$)$_3$ which has been prepared according to literature; see Bo Li "Heterometallic Carboxylates Incorporating Bismuth", PhD Thesis, State University of New York at Albany, Chair M. Petrukhina 2007, UMI Number 3277252, and Vera Reiland "Chemie und Koordinationschemie von Bismuttri-fluoracetat und verwandten Verbindungen" [Chemistry and Coordination Chemistry of Bismuth Trifluoroacetate and Related Compounds], Thesis D368, University of Kaiserslautern 2000.

Vaporization

ITO-prestructured glass substrates were subjected to an oxygen plasma treatment for 10 min and then subsequently transferred as quickly as possible to the vaporizer. The vaporizer was transferred into an argon glovebox in which the oxygen and water concentration was less than 2 ppm.

All the vaporizations were conducted at a vacuum of less than $2 \times 10^{-6}$ mbar base pressure (the pressure then rises in the course of vaporization).

First of all, both the matrix material and doping material were heated to just below the vaporization point, then heating was continued until constant vaporization was observable.

The overall vaporization rate was about 1 Å/s, with the vaporization rate of the doping material set via the vaporization rate of the matrix material.

Once the shutters had been closed, the system was cooled to 40° C. and flooded with argon, the mask for the deposition of the cathode was changed, and then the system was evacuated again.

The electrode was formed of a 150 nm-thick layer of aluminum, which was applied at an initial vaporization rate of 0.5 Å/s, which was increased gradually to 5 Å/s.

FIGS. 4 to 7 relate to Bi(O$_2$CCF$_3$)$_3$-doped and undoped HTM-014 (matrix material, from Merck KGaA). In these cases, 200 nm-thick layers of HTM-014 (Merck KGaA) on the one hand, and of HTM-014 doped with 15% Bi(O$_2$CCF$_3$)$_3$ on the other hand, were produced.

FIG. 4 shows current density against voltage applied for the two materials. Even in the case of the doped layer, an increase in current density against voltage applied is observed.

Figure 5:
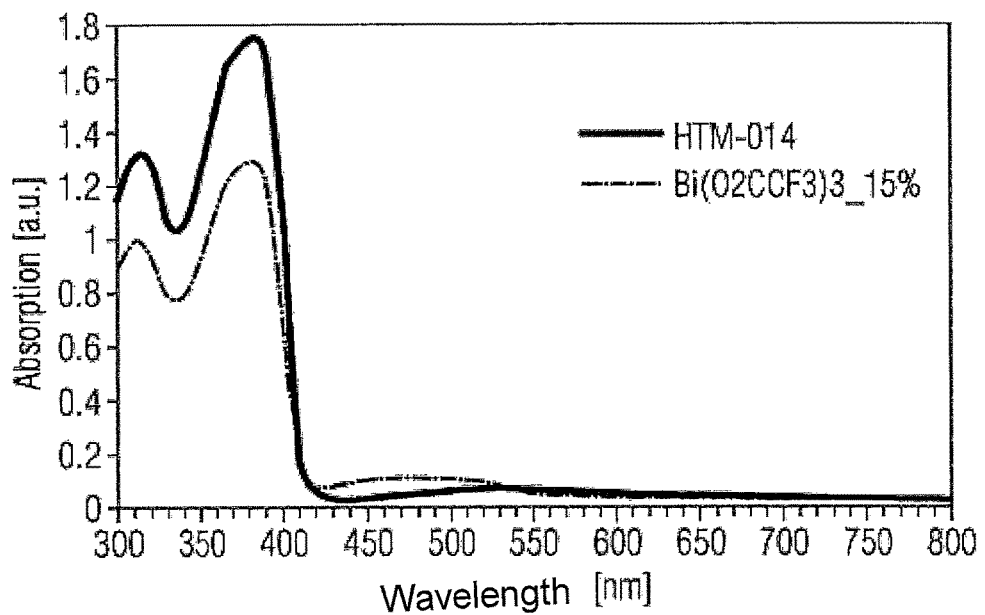
FIG. 5 is a graph of absorption against wavelength for the materials from FIG. 4.
Figure 6:
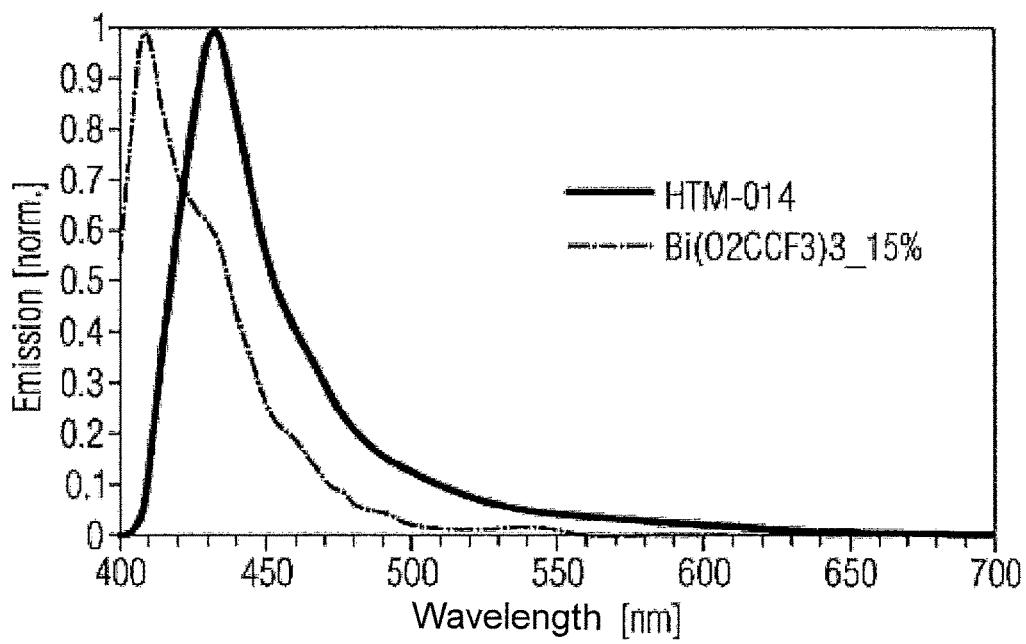
FIG. 6 is a graph of photoluminescence against wavelength for the materials from FIG. 4.
Figure 7:
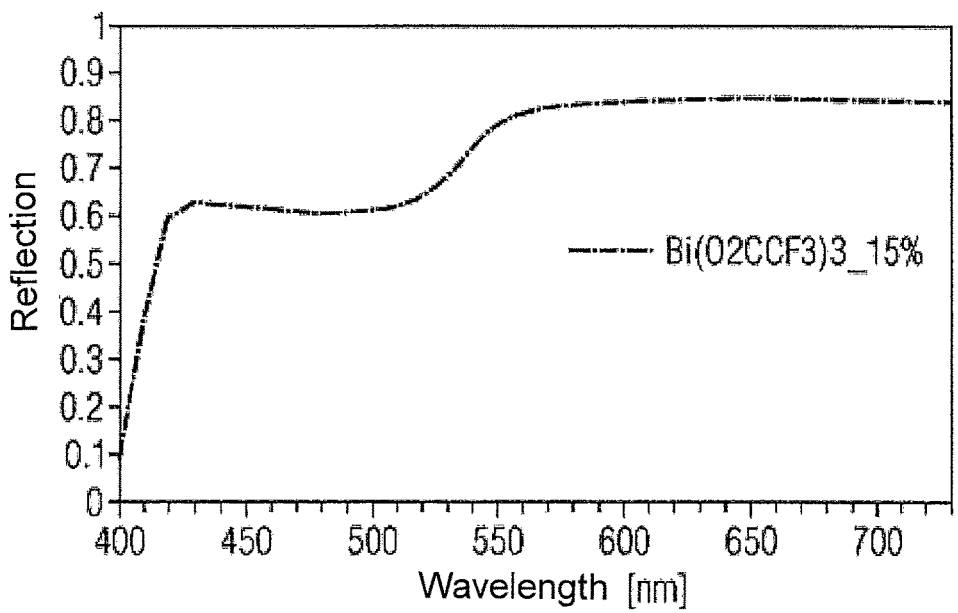
FIG. 7 is a graph of reflection against wavelength for the doped material from FIG. 4.

To study the optical properties of the proposed dopant material, absorption, photoluminescence and reflection were measured (FIGS. 5 to 7). It can be seen that the complexes are virtually transparent, which makes them suitable for use in (opto)electronic components.

Example II

Example II relates to $Bi(O_2CC_6H_2(2,3,4-F_3))_3$, which was prepared as follows:

A 50 mL Schlenk flask was charged with 0.251 g (0.57 mmol) of triphenylbismuth(III), followed by 10-15 mL of freshly distilled benzene, and an excess (about 3 mmol) of 2,3,4-trifluorobenzoic acid was added. The mixture is heated under reflux for one hour and then cooled to room temperature; subsequently, the solvent is drawn off under reduced pressure until a white solid precipitates out. The crude product (yield 85-88%) is washed with a little hexane and dried under reduced pressure overnight. Purification can be accomplished by sublimation.

In analogy to example I, four layers, one of an undoped matrix material (HTM-014, Merck), and HTM-014 layers doped with 5%, 13% and 15% $Bi(O_2CC_6H_2(2,3,4-F_3))_3$, were applied. The layer thickness was 200 nm in each case.

Figure 8:
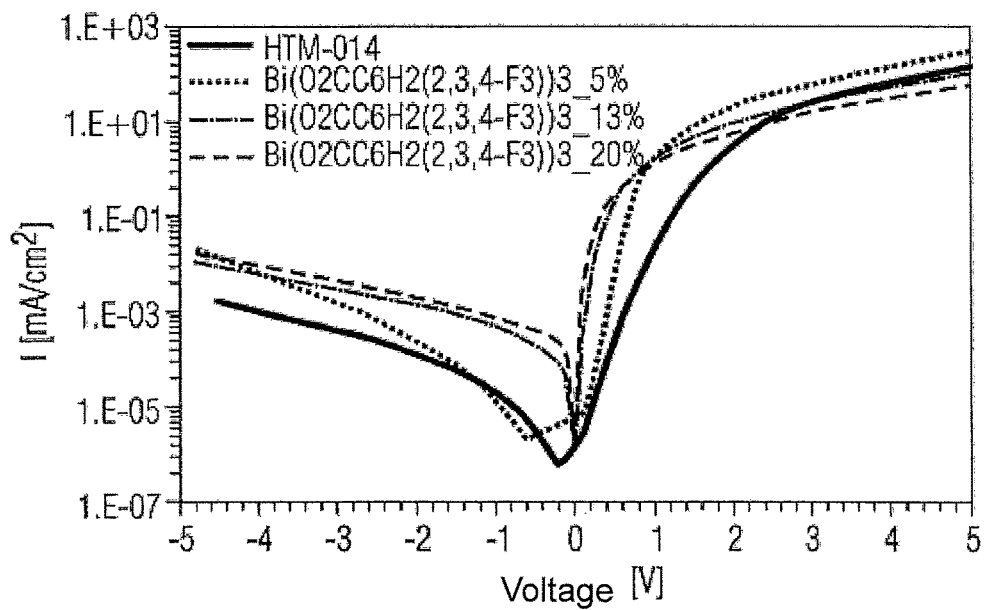
FIG. 8 is a graph of current density against voltage for an undoped matrix material and for several doped matrix materials in a second embodiment.

FIG. 8 shows current density against voltage applied for the three materials. Even in the case of the layer with 5% doping, an increase in current density against voltage applied is observed.

Figure 9:
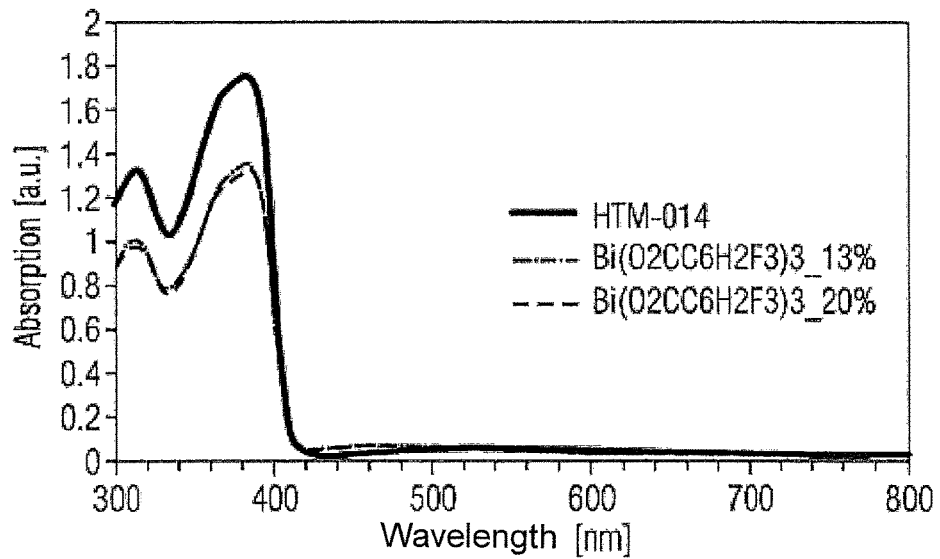
FIG. 9 is a graph of absorption against wavelength for the materials from FIG. 8.
Figure 10:
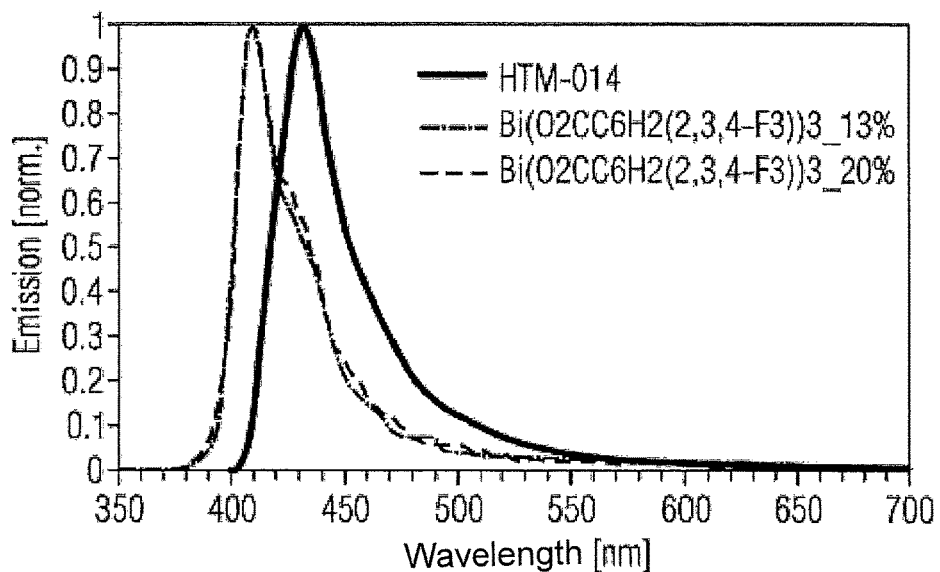
FIG. 10 is a graph of photoluminescence against wavelength for the doped materials from FIG. 8.
Figure 11:
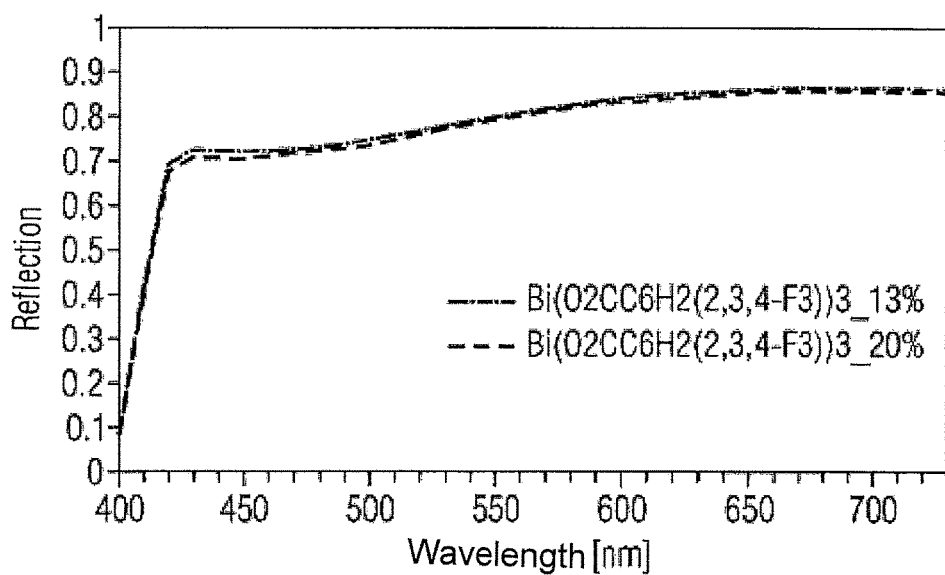
FIG. 11 is a graph of reflection against wavelength for the materials from FIG. 8.

To study the optical properties of the dopant material, absorption, photoluminescence and reflection were measured (FIGS. 9 to 11). It can be seen that the complexes are virtually transparent, which makes them suitable for use in (opto)electronic components.

Example III

In the course of a solvent process, a majority charge carrier component is produced, using HIL-012 (matrix material, from Merck KGaA) as polymeric hole conductor and the metal complexes $Bi(O_2C_2P_3)_3$ and BipFbz as dopants.

To produce an undoped hole conductor, a 2% by weight solution of the HIL-012 in anisole and xylene (volume ratio of the solvents 1:1) is applied by a spin-coater to an ITO-coated glass plate. The application is effected for 40 s with a spin speed of 1200 rpm (revolutions per minute) and, after drying at 120° C. for 1 h standard pressure, a 120 nm-thick HIL-012 layer is obtained. For the upper electrode, by a vacuum vaporization process, a 200 nm-thick aluminum layer is applied.

The layers doped with the metal complexes are produced analogously, except that the solutions admixed with the bismuth tris(trifluoroacetate) $Bi(O_2C_2F_3)_3$ or bismuth tris(pentafluorobenzoate) (BipFbz) dopants are processed. The total solids content in these embodiments totals 2% by weight, and the proportion of the dopants in the total solids content is 15% by weight.

The parameters for the spin-coating are found to be 1500 rpm for the element with $Bi(O_2C_2F_3)_3$ as dopant, and 1000 rpm for the element with BipFbz. in total, coating is effected for a period of 40 s, and the layer thickness after drying using the abovementioned parameters is 100 nm for both elements.

The measurements in each case are effected on elements of size 4 mm$^2$.

Figure 12:
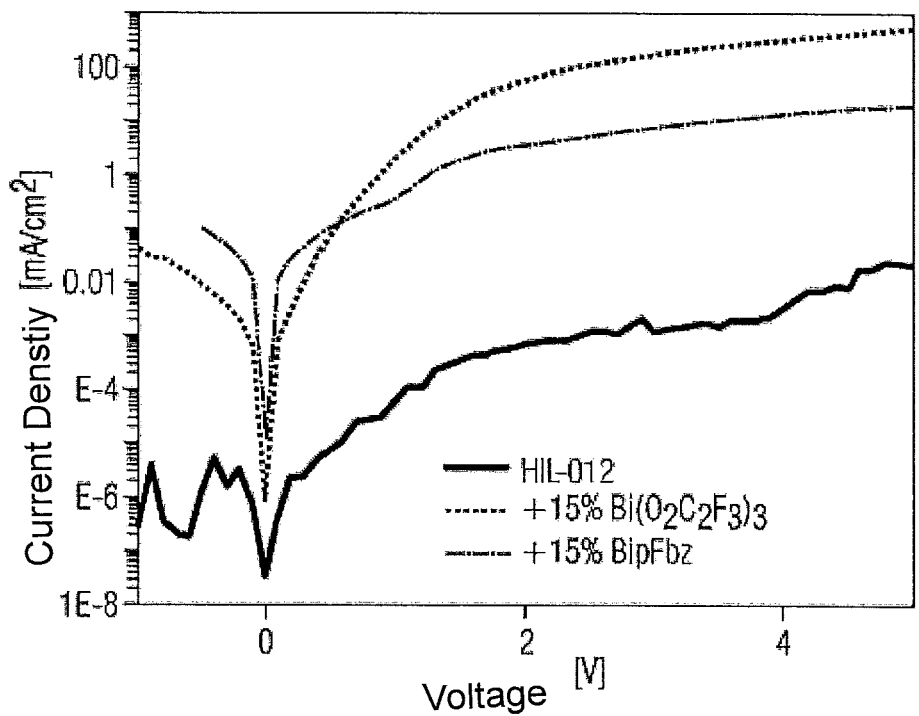
FIG. 12 is a graph of current density against voltage for an undoped matrix material and for several doped matrix materials in a third embodiment.

FIG. 12 shows the current density-voltage characteristics obtained for the different components in this example. It can be clearly seen that the doping results in an increase in conductivity by several orders of magnitude.

Example IV

In the course of a solvent process, a majority charge carrier component is produced, using spiro-TTB as polymeric hole conductor and the metal complexes $Bi(O_2C_2F_3)_3$ and BipFbz as dopants.

The processing of the dopants with the spiro-TTB hole conductor material, a "small molecule", is effected in an analogous manner to example III. For the production of 100 nm-thick layers, a total of 3.5% by weight solutions are produced (anisole:xylene solvent mixture, ratio 1:2), which contain 1.6 mol %, 2 mol % and 10 mol % of dopant, based on the amount of matrix material. The solutions are spun on at 750 rpm for 40 s and dried at 120° C. for 1 h.

Figure 13:
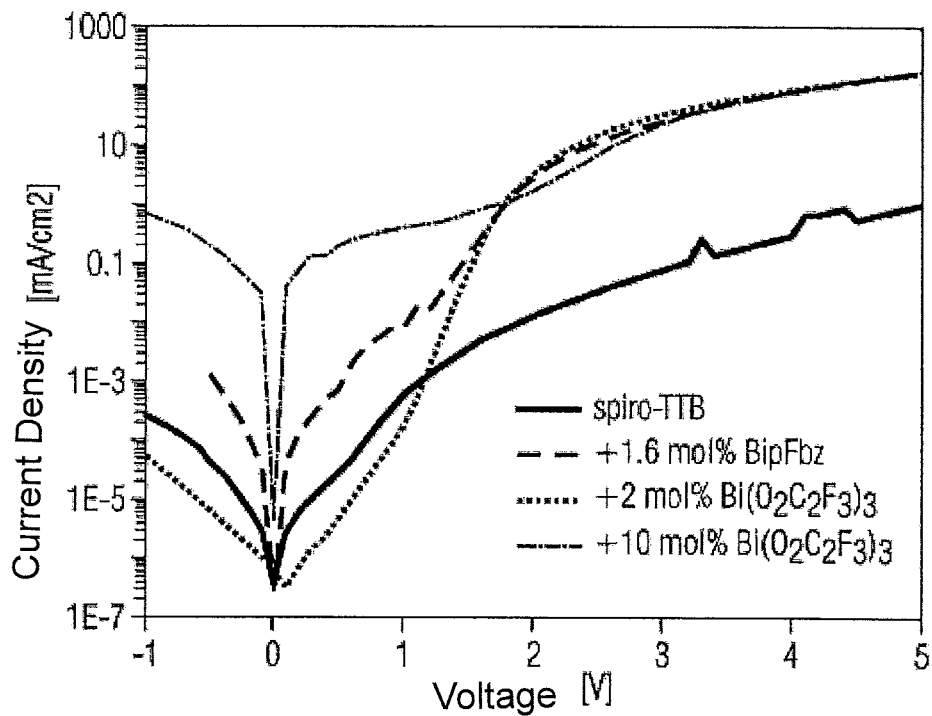
FIG. 13 is a graph of current density against voltage for an undoped matrix material and for several doped matrix materials in a fourth embodiment.

FIG. 13 shows the current density-voltage characteristics obtained for the different components in this example. The doping can again achieve a very distinct increase in conductivity compared to the pure hole conductor material. In addition, it is found that about 10 mol % of doping is necessary to achieve a sufficient influence on conductivity.

Example V

The undoped and doped hole conductor layers described in example III are incorporated into red OLEDs. The red OLEDs have the following layer structure: glass/ITO/100 nm HTL varied/10 nm NPB/20 nm emitter layer of 20% NPB, 70% TPBi, 10% ADS076/60 nm TPBi/0.7 nm LiF/200 nm Al.

Figure 14:
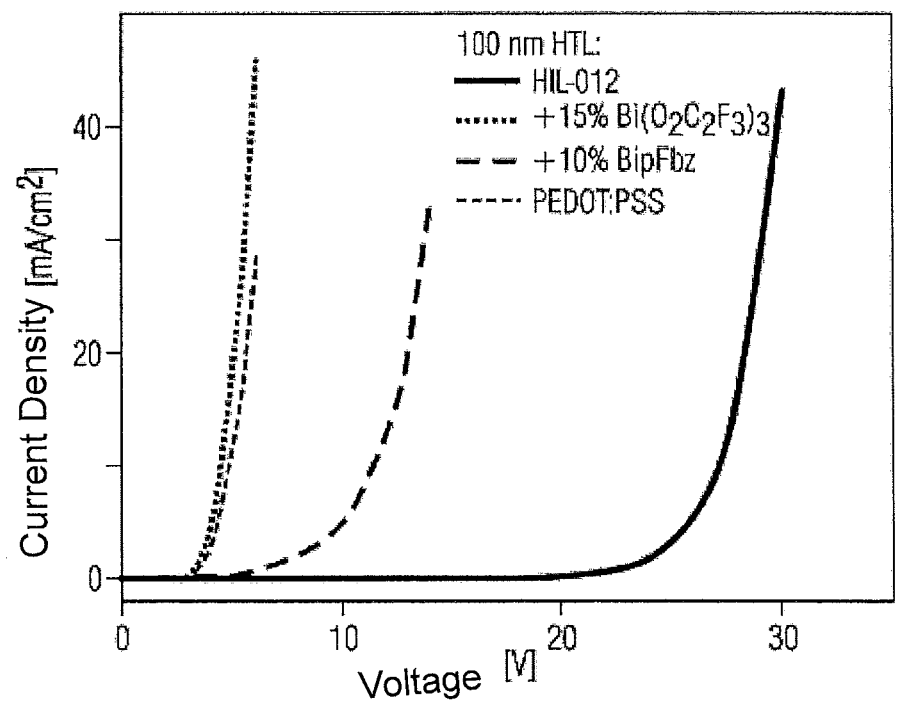
FIG. 14 is a graph of current density against voltage for an undoped matrix material and for several doped matrix materials in a fifth embodiment.
Figure 15:
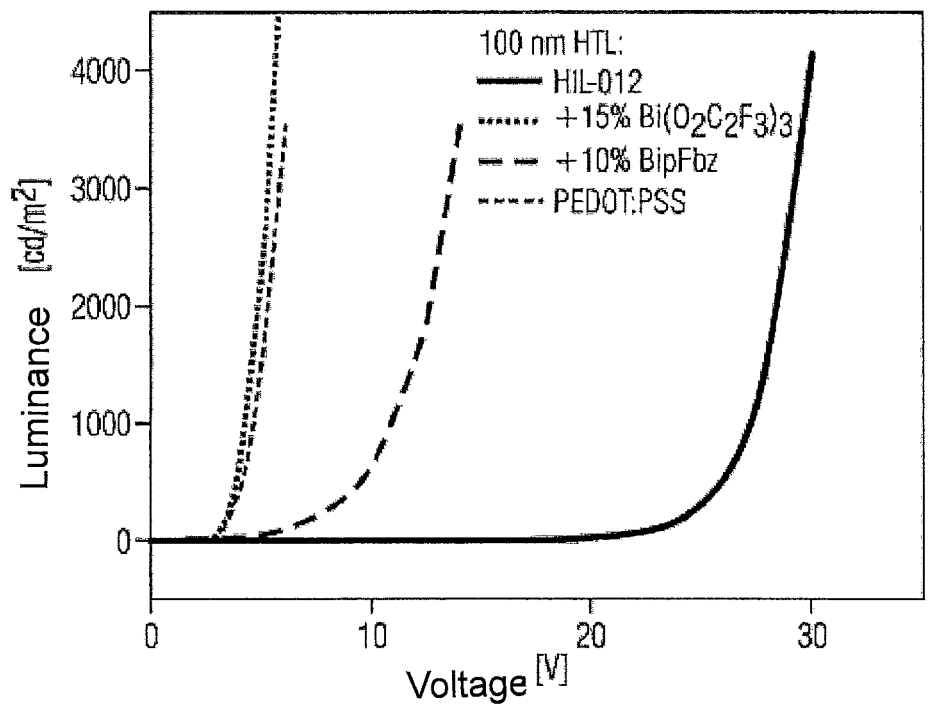
FIG. 15 is a graph of luminescence against voltage for the doped materials from FIG. 14.

As dopants, bismuth tris(trifluoroacetate) $Bi(O_2C_2F_3)_3$ and bismuth tris(pentafluorobenzoate) (BipFbz) are used in the concentrations stated in FIG. 14 and FIG. 15. It is found that the OLEDs obtained by a solvent process, with regard to luminance (FIG. 15) and the current-voltage characteristic (FIG. 14), are better than reference OLEDs comprising PEDOT-PSS.

Example VI

Figure 16:
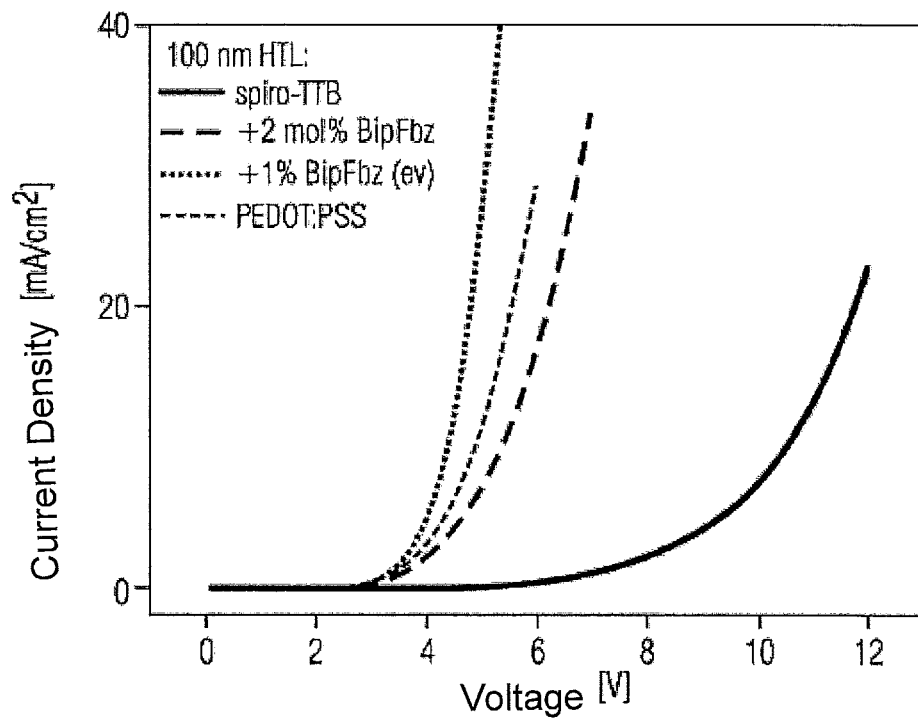
FIG. 16 is a graph of current density against voltage for an undoped matrix material and for several doped matrix materials in a sixth embodiment.
Figure 17:
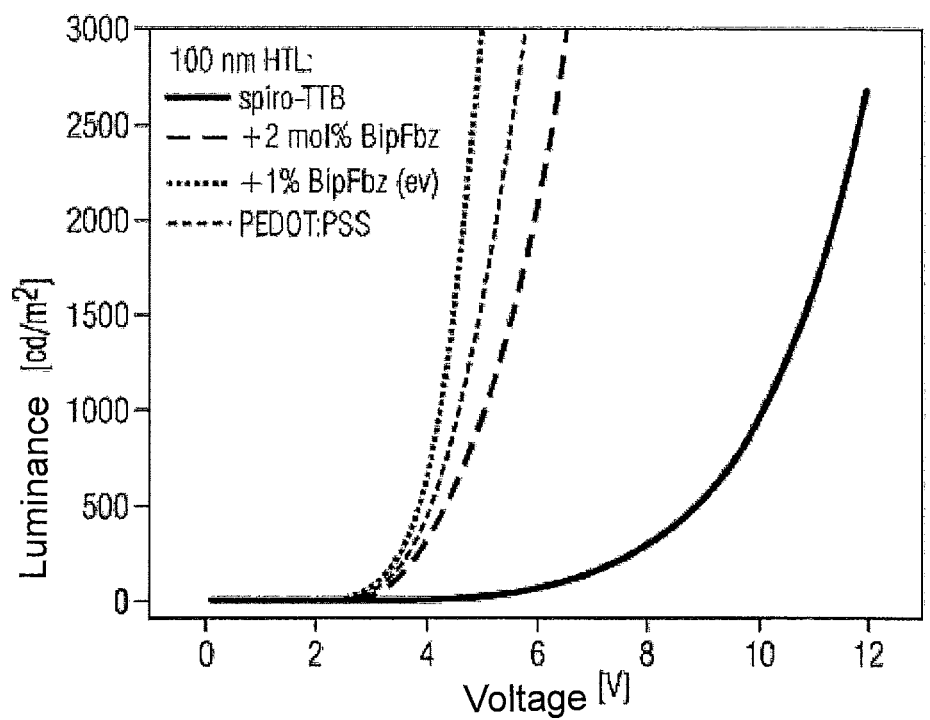
FIG. 17 is a graph of luminescence against voltage for the doped materials from FIG. 16.

Instead of the HIL-012-based HIL from example V, spiro-TTB is utilized as hole conductor and doped with BipFbz. spiro-TTB and BipFbz can be prepared both by the solvent process (characteristic identified by BipFbz) and by the vaporization process (characteristic identified by BipFbz (ev)). The characteristic current density-voltage characteristic and luminance-voltage characteristic are depicted in FIGS. 16 and 17. It is found that the properties of layers produced by the vaporization process are better than those deposited from solution. However, the differences are small.

Example VII

The doped hole conductor layers produced in examples III and IV can also be utilized as hole conductor layers for organic solar cells, especially those with p-i-n structure.

The individual combinations of the constituents and of the features of the executions already mentioned are illustrative; the exchange and the substitution of these teachings for other teachings present in this publication are likewise explicitly contemplated with the publications cited. It will be apparent to the person skilled in the art that variations, modifications and other executions which are described here can likewise occur, without departing from the idea and the scope.

The invention has been described in detail with particular reference to preferred embodiments thereof and examples, but it will be understood that variations and modifications can be effected within the spirit and scope of the invention covered by the claims which may include the phrase "at least one of A, B and C" as an alternative expression that means one or more of A, B and C may be used, contrary to the holding in Superguide v. DIRECTV, 69 USPQ2d 1865 (Fed. Cir. 2004).

The invention claimed is:

1. An organic electronic component comprising:
   a hole transport layer comprising a matrix doped with a p-dopant, the p-dopant being a main group metal complex of a metal from groups 13 to 15, the metal complex containing at least one ligand L of the following structure:

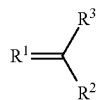

where each of $R^1$ and $R^2$ is selected from the group consisting of oxygen, sulfur, selenium, NH and $NR^4$, where $R^4$ is an alkyl or an aryl group and may be bonded to $R^3$; and
   where $R^3$ is selected from the group consisting of halo-substituted alkyl groups, aryl groups, and heteroaryl groups.

2. The component as claimed in claim 1, wherein the metal is selected from the group consisting of bismuth, tin and mixtures of bismuth and tin.

3. The component as claimed in claim 1, wherein the metal complex has a structure MLm with M=metal, L=ligand and m=1 to 10, where all ligands L are independent of one another when m>1.

4. The component as claimed in claim 1, wherein R3 is represented by the following formula:

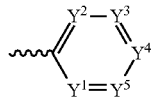

where $Y^1$-$Y^5$ are each independently selected from the group consisting of C—F and C—H.

5. The component as claimed in claim 1, wherein R3 is represented by the following formula:

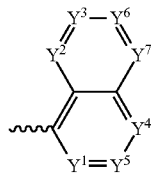

where $Y^1$-$Y^7$ are each independently selected from the group consisting of C—F and C—H.

6. The component as claimed in claim 1, wherein $R^3$ is represented by the following formula:

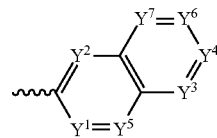

where $Y^1$-$Y^7$ are each independently selected from the group consisting of C—F and hd —H.

7. The component as claimed in claim 1, wherein the metal complex further contains at least one ligand selected from the group consisting of unsubstituted organic carboxylic acids, partially fluorinated organic carboxylic acids and perfluorinated organic carboxylic acids.

8. The component as claimed in claim 1, wherein the metal complex further contains at least one ligand selected from the group consisting of unsubstituted acetic acid, partially fluorinated acetic acids and perfluorinated acetic acids.

9. The component as claimed in claim 1, wherein where $R^3$ is selected from the group consisting of alkyl groups, long-chain alkyl groups, alkoxy groups, long-chain alkoxy groups, cycloalkyl groups, haloalkyl groups, aryl groups, arylenes, haloaryl groups, and heteroaryl groups, heteroarylenes, heterocycloalkylenes, heterocycloalkyl groups, haloheteroaryl groups, alkenyl groups, haloalkenyl groups, alkynyl groups, haloalkynyl groups, ketoaryl groups, haloketoaryl groups, ketoheteroaryl groups, ketoalkyl groups, haloketoalkyl groups, ketoalkenyl groups, haloketoalkenyl groups, where one or more non-adjacent CH2 groups in suitable radicals may independently be replaced by:
   —O—, —S—, —NH—, —NR°—, —SiR°R°°—, —CO—, —COO—, —OCO—, —OCO—O—, —SO₂—, —S—CO—, —CO—S—, —CY1=CY2 or —C≡C—, in such a way that no oxygen and/or sulfur atoms are bonded directly to one another, or
   an aryl group or a heteroaryl group containing 1 to 30 carbon atoms in which terminal CH₃ groups are regarded as CH₂ groups, CH₂—H.

10. A method comprising:
    using a matrix material for a hole transport layer defining a component of an electronic device, the matrix material of the hole transport layer being doped with a p-dopant, the p-dopant being a main group metal complex of a metal from groups 13 to 16, the metal complex containing at least one ligand L of the following structure:

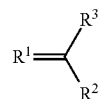

where each of $R^1$ and $R^2$ is selected from the group consisting of oxygen, sulfur, selenium, NH and $NR^4$, where $R^4$ is an alkyl or an aryl group and may be bonded to $R^3$; and
    where $R^3$ is selected from the group consisting of halo-substituted alkyl groups, aryl groups, and heteroaryl groups.

11. The method as claimed in claim 10, wherein the electronic device is an organic light emitting diode, and the matrix material is used as a hole transport layer in the organic light emitting diode.

12. The method as claimed in claim 10, wherein the electronic device is a solar cell, and the matrix material is used as a p-doped layer in the solar cell.

13. The method as claimed in claim 10, wherein the electronic device is an organic field effect transistor, and the matrix material is used as an organic semiconductor layer in the organic field effect transistor.

14. The method as claimed in claim 10, wherein where $R^3$ is selected from the group consisting of alkyl groups, long-chain alkyl groups, alkoxy groups, long-chain alkoxy groups, cycloalkyl groups, haloalkyl groups, aryl groups, arylenes, haloaryl groups, and heteroaryl groups, heteroarylenes, heterocycloalkylenes, heterocycloalkyl groups, haloheteroaryl groups, alkenyl groups, haloalkenyl groups, alkynyl groups, haloalkynyl groups, ketoaryl groups, haloketoaryl groups, ketoheteroaryl groups, ketoalkyl groups, haloketoalkyl groups, ketoalkenyl groups, haloketoalkenyl groups, where one or more non-adjacent CH2 groups in suitable radicals may independently be replaced by:

—O—, —S—, —NH—, —NR°—, —SiR°R°°—, —CO—, —COO—, —OCO—, —OCO—O—, —SO$_2$—, —S—CO—, —CO—S—, —CY1═CY2 or —C≡C—, in such a way that no oxygen and/or sulfur atoms are bonded directly to one another, or an aryl group or a heteroaryl group containing 1 to 30 carbon atoms in which terminal CH$_3$ groups are regarded as CH$_2$ groups, CH$_2$—H.

15. An organic electronic component comprising:
a matrix containing a p-dopant, the p-dopant being a main group metal complex of a metal from groups 13 to 15, the metal complex containing at least one ligand L of the following structure:

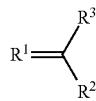

where each of $R^1$ and $R^2$ is selected from the group consisting of oxygen, sulfur, selenium, NH and $NR^4$, where $R^4$ is an alkyl or an aryl group and may be bonded to $R^3$; and where $R^3$ is represented by one of the following formulas:
(a)

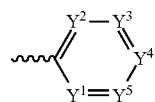

where $Y^1$-$Y^5$ are each independently selected from the group consisting of C—F and C—H; or
(b)

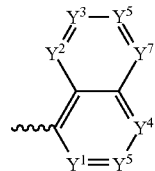

where $Y^1$-$Y^7$ are each independently selected from the group consisting of C—F and C—H; or
(c)

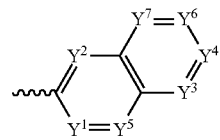

where $Y^1$-$Y^7$ are each independently selected from the group consisting of C—F and C—H.

16. The component as claimed in claim 15, wherein the metal is selected from the group consisting of bismuth, tin and mixtures of bismuth and tin.

17. The component as claimed in claim 15, wherein the metal complex has a structure MLm with M=metal, L=ligand and m=1 to 10, where all ligands L are independent of one another when m>1.

18. The component as claimed in claim 15, wherein the metal complex further contains at least one ligand selected from the group consisting of unsubstituted organic carboxylic acids, partially fluorinated organic carboxylic acids and perfluorinated organic carboxylic acids.

19. The component as claimed in claim 15, wherein the metal complex further contains at least one ligand selected from the group consisting of unsubstituted acetic acid, partially fluorinated acetic acids and perfluorinated acetic acids.

* * * * *

UNITED STATES PATENT AND TRADEMARK OFFICE
CERTIFICATE OF CORRECTION

PATENT NO. : 10,411,197 B2
APPLICATION NO. : 14/406041
DATED : September 10, 2019
INVENTOR(S) : Anna Maltenberger et al.

Page 1 of 1

It is certified that error appears in the above-identified patent and that said Letters Patent is hereby corrected as shown below:

On the Title Page

(71) Applicant,
"SIEMENS AKTIENGESELLSCHAFT, MUNICH (DE)..." ---Change to--- "...SIEMENS AKTIENGESELLSCHAFT, MUNICH (DE); OSRAM OLED GMBH, REGENSBURG (DE)..."

In the Claims

Column 18,
Claim 6, Line 10, "...group consisting of C-F and hd-H ..." ---Change to--- "...group consisting of C-F and C-H..."

Column 20,

Claim 15, Line 12, "...(b) 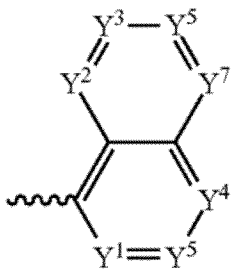 ..." ---Change to--- "...(b) 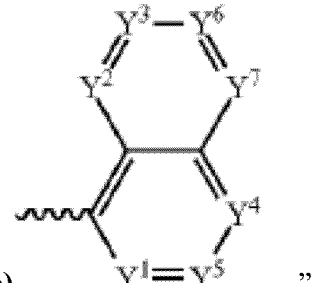 ..."

Signed and Sealed this
Nineteenth Day of May, 2020

Andrei Iancu
*Director of the United States Patent and Trademark Office*